US009987058B2

(12) United States Patent
Suh et al.

(10) Patent No.: US 9,987,058 B2
(45) Date of Patent: Jun. 5, 2018

(54) ORTHOPEDIC ANCHOR ASSEMBLY

(71) Applicant: GLOBUS MEDICAL, INC., Audubon, PA (US)

(72) Inventors: Sean Suh, Morganville, PA (US); Jon Suh, Ambler, PA (US)

(73) Assignee: GLOBUS MEDICAL INC., Audubon, PA (US)

( * ) Notice: Subject to any disclaimer, the term of this patent is extended or adjusted under 35 U.S.C. 154(b) by 0 days. days.

(21) Appl. No.: 15/219,332

(22) Filed: Jul. 26, 2016

(65) Prior Publication Data

US 2016/0331424 A1 Nov. 17, 2016

Related U.S. Application Data

(63) Continuation of application No. 13/548,641, filed on Jul. 13, 2012, now Pat. No. 9,421,052, which is a continuation of application No. 12/371,437, filed on Feb. 13, 2009, now Pat. No. 8,241,339.

(51) Int. Cl.
*A61B 17/80* (2006.01)
*A61B 17/86* (2006.01)
*A61B 17/70* (2006.01)

(52) U.S. Cl.
CPC ...... *A61B 17/8038* (2013.01); *A61B 17/7001* (2013.01); *A61B 17/8033* (2013.01); *A61B 17/8052* (2013.01); *A61B 17/8605* (2013.01); *A61B 2017/8655* (2013.01)

(58) Field of Classification Search
CPC .................................................. A61B 17/8038
See application file for complete search history.

(56) References Cited

U.S. PATENT DOCUMENTS

| | | | |
|---|---|---|---|
| 3,074,134 A | 1/1963 | Buechler | |
| 4,484,570 A | 11/1984 | Sutter et al. | |
| 5,681,311 A | 10/1997 | Foley et al. | |
| 5,902,303 A * | 5/1999 | Eckhof | A61B 17/8872 606/309 |
| 6,117,173 A | 9/2000 | Taddia et al. | |
| 6,235,033 B1 | 5/2001 | Brace et al. | |
| 6,517,543 B1 | 2/2003 | Berrevoets et al. | |
| 6,613,053 B1 | 9/2003 | Collins et al. | |
| 7,048,739 B2 | 5/2006 | Konieczynski et al. | |
| 7,063,701 B2 | 6/2006 | Michelson | |
| 7,785,327 B1 | 8/2010 | Navarro et al. | |
| 2003/0199876 A1 | 10/2003 | Brace et al. | |
| 2006/0167456 A1 | 7/2006 | Johnston et al. | |
| 2006/0264936 A1 | 11/2006 | Partin et al. | |
| 2007/0288025 A1 | 12/2007 | Peukert et al. | |
| 2008/0288000 A1 | 11/2008 | Cawley | |
| 2009/0192553 A1 | 7/2009 | Maguire et al. | |

(Continued)

*Primary Examiner* — Samuel Hanna

(57) ABSTRACT

In an exemplary embodiment, the present invention provides an anchor assembly that can be used for the fixation or fastening of orthopedic devices or instruments to bone tissue. In particular, the present invention preferably provides a variable angle or fixed angle anchor assembly that is able to securely connect the orthopedic device to bone tissue even when there is a variance in the angle and position of the assembly with respect to the device. Furthermore, in an exemplary embodiment, the present invention provides an anchor assembly having a locking mechanism that will quickly and easily lock the anchor assembly with respect to the orthopedic device.

14 Claims, 2 Drawing Sheets

(56) References Cited

U.S. PATENT DOCUMENTS

| | | | |
|---|---|---|---|
| 2009/0248087 | A1 | 10/2009 | Lewis et al. |
| 2011/0270326 | A1 | 11/2011 | Black et al. |
| 2012/0303071 | A1 | 11/2012 | Black et al. |
| 2013/0096633 | A1 | 4/2013 | Black et al. |

* cited by examiner

ORTHOPEDIC ANCHOR ASSEMBLY

CROSS REFERENCE TO RELATED APPLICATIONS

This Patent Application is a continuation of U.S. patent application Ser. No. 13/548,641, filed Jul. 13, 2012, which is a continuation of U.S. patent application Ser. No. 12/371,437, filed Feb. 13, 2009, now U.S. Pat. No. 8,241,339, all of which are incorporated herein by reference in their entireties for all purposes.

FIELD OF THE INVENTION

The present invention is directed to a bone fixation assembly and, in particular, to an anchor assembly for securing an orthopedic device to bone tissue.

BACKGROUND OF THE INVENTION

As is known in the field of orthopedic surgery, and more specifically spinal surgery, bone anchors may be used for fixation or for the fastening of orthopedic devices or instruments to bone tissue. An exemplary use of bone anchors may include using the bone anchors to fasten an orthopedic device, such as a bone plate, a spinal rod, or a spinal spacer, to a vertebral body for the treatment of a deformity or defect in a patient's spine. Focusing on the bone plate example, bone anchors can be secured to a number of vertebral bodies and a bone plate can then be connected to the vertebral bodies via the bone anchors to fuse a segment of the spine. In another example, bone anchors can be used to fix the location of a spinal spacer once the spacer is implanted between adjacent vertebral bodies. In yet another example, bone anchors can be fastened to a number of vertebral bodies to anchor a spinal rod in place along a spinal column to treat a spinal deformity.

In each of these exemplary uses, a plurality of bone anchors are needed to fasten the orthopedic device to the area of treatment. In addition, depending on the extent of the disease or size of the defect to be treated, it is possible that several orthopedic devices each requiring a plurality of bone anchors may be required. Accordingly, the fastening of the orthopedic implants to the area of treatment can become a time consuming and even difficult task.

As such, there exists a need for bone anchors that can quickly and securely fasten an orthopedic device to the area of treatment.

SUMMARY OF THE INVENTION

In a preferred embodiment, the present invention provides an anchor assembly that can be used for the fixation or fastening of orthopedic devices or instruments to bone tissue. In particular, the present invention preferably provides a variable angle or fixed angle anchor assembly that is able to securely connect the orthopedic device to bone tissue even when there is a variance in the angle and position of the assembly with respect to the device. Furthermore, in a preferred embodiment, the present invention provides an anchor assembly having a locking mechanism that will quickly and easily lock the anchor assembly with respect to the orthopedic device.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
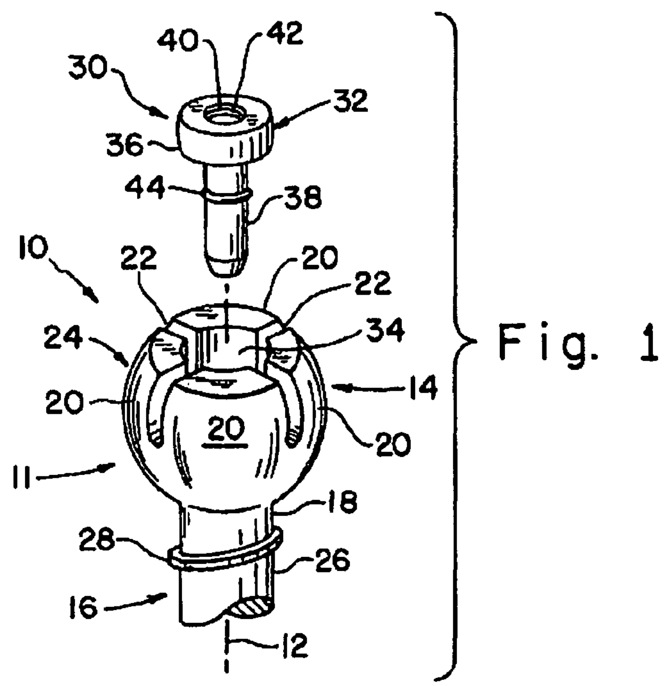
FIG. 1 is an exploded partial perspective view of one embodiment of an anchor assembly.

The following description of the preferred embodiment(s) is merely exemplary in nature and is in no way intended to limit the invention, its application, or uses.

With reference to FIGS. 1-4, a preferred embodiment of an anchor assembly 10 is illustrated. The anchor assembly 10 preferably includes an anchor 11 and a locking mechanism 30. Although the anchor 11 will be discussed in the context of an orthopedic screw, it is contemplated that the anchor 11 can be any type of anchoring element including, but not limited to, a hook, a pin, or a nail. In a preferred embodiment, the anchor 11 includes, concentric to a longitudinal axis 12, a head portion 14, a neck portion 18 and a shank portion 16. The head portion 14 connects to the shank portion 16 through the neck portion 18. The anchor assembly 10 is preferably constructed from any biocompatible material including, but not limited to, stainless steel alloys, titanium, titanium based alloys, or polymeric materials.

In a preferred embodiment, the head portion 14 of the anchor 11 has a generally spherical shape and includes at least one resilient finger element 20. In another preferred embodiment, the head portion 14 includes four resilient finger elements 20. Preferably, located on either side of the resilient finger element 20 is an elongated groove 22. The grooves 22 may be configured and dimensioned to correspond with the end of a driving instrument (not shown) designed to engage the anchor 11, and consequently the anchor assembly 10.

Figure 4:
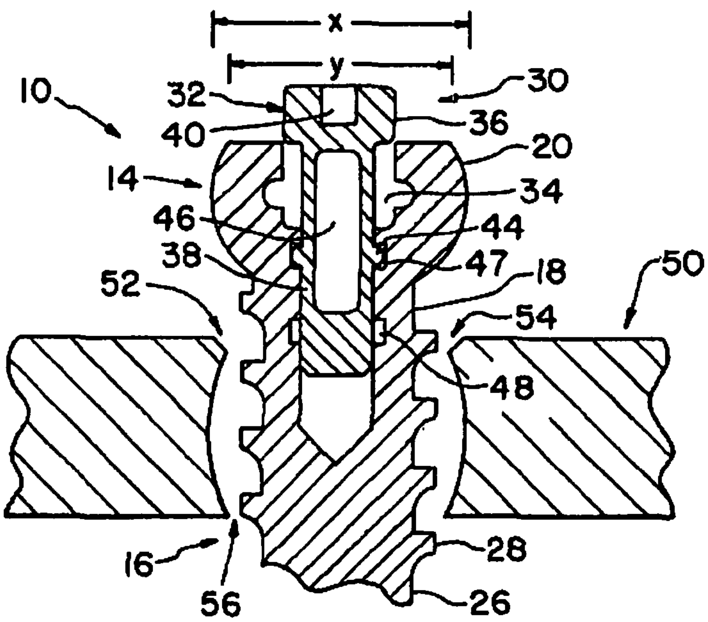
FIG. 4 is a partial cross-sectional view of the anchor assembly shown in FIG. 1.

As best shown in FIG. 4, the generally spherical shape of the head portion 14 is configured and dimensioned to be received within a correspondingly shaped cavity 52 in an orthopedic device 50 which may be part of a spinal fixation system. In an exemplary embodiment, the orthopedic device 50 is a bone plate, but the orthopedic device can be any device, such as a spinal rod "tulip" style holder or a spinal spacer. The shape of the head portion 14 and the correspondingly shaped cavity 52 allows the anchor assembly 10 to pivot, rotate and/or move with respect to the orthopedic device 50. In another embodiment, instead of allowing the anchor assembly 10 to pivot, rotate and/or move with respect to the orthopedic device 50, the head portion 14 and the correspondingly shaped cavity 52 maybe configured and dimensioned to keep the anchor assembly 10 in a fixed position. In an exemplary use, the head portion 14 of the anchor 11 is received in the cavity 52 of the orthopedic device 50 and the anchor assembly 10 is pivoted, rotated or moved until the desired orientation with respect to the orthopedic device 50 is met. The anchor assembly 10 is then locked in place, which is discussed in detail below, in the cavity 52 of the orthopedic device 50. In a preferred embodiment, the head portion 14 also includes texturing 24 that extends along at least a portion of the head portion 14. The texturing 24 on the head portion 14 provides additional frictional surfaces which aid in locking the anchor assembly 10 in place with respect to the orthopedic device 50.

Turning back to FIGS. 1-3, in a preferred embodiment, the neck portion 18 of the anchor 11 integrally connects the head portion 14 with the shank portion 16. The diameter of the neck portion 18 is preferably dimensioned to match the minor diameter of the anchor 11. By having the diameter of the neck portion 18 dimensioned at least as large as the minor diameter of the anchor 11, the overall rigidity and strength of the anchor 11 is increased.

In a preferred embodiment, the shank portion 16 of the anchor 11 includes a shaft 26 surrounded at least in part by a thread portion 28. The diameter of the shaft 26 is the minor diameter of the anchor assembly 10. In a preferred embodiment, the diameter of the shaft 26 remains generally constant from a proximal end of the shaft 26 toward a distal end of the shaft 26. The constant diameter of a majority portion of the shaft 26 allows for optimal anchor positioning when the anchor assembly 10 is inserted into a predetermined area in the bone tissue. The constant diameter also allows for varying the depth positioning of the anchor assembly 10 in the bone. For example, if a surgeon places the anchor assembly 10 into bone tissue at a first depth and decides the placement is more optimal at a second, shallower depth, the anchor assembly 10 can be backed out to the second depth and still remain fixed in the bone. In another embodiment, the diameter of the shaft 26 may vary along its length, including increasing in diameter from the proximal end to the distal end or decreasing in diameter from the proximal end to the distal end.

Figure 2:
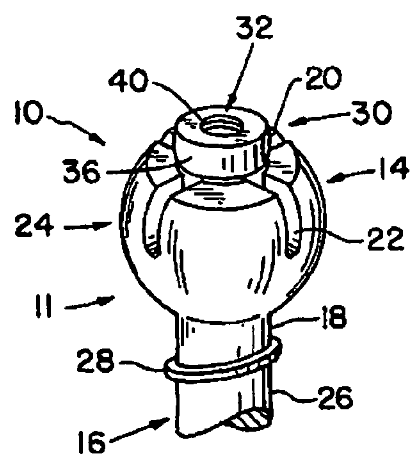
FIG. 2 is a partial perspective view of the anchor assembly shown in FIG. 1.
Figure 3:
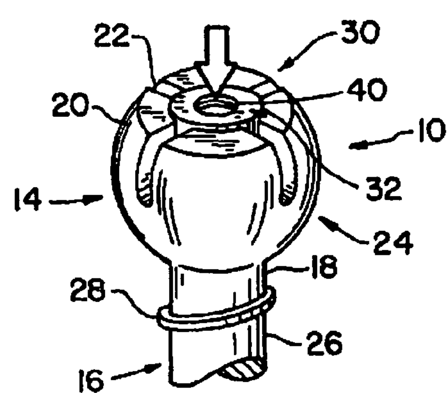
FIG. 3 is partial perspective view of the anchor assembly shown in FIG. 1.

With continued reference to FIGS. 1-3, the thread portion 28 surrounding the shaft 26 extends, in a preferred embodiment, from the distal end of the shaft 26 to the neck portion 18. In another preferred embodiment, the thread portion 28 may extend along only a portion of shaft 26. The thread portion 28 is preferably a Modified Buttress thread but the thread can be any other type of threading that is anatomically conforming, including, but not limited to Buttress, Acme, Unified, Whitworth and B&S Worm threads.

In a preferred embodiment, the diameter of the thread portion 28 decreases towards the distal end of the anchor 11. By having a decreased diameter thread portion 28 near the distal end of the anchor 11, the anchor 11 can be self-starting. In another preferred embodiment, anchor 11 may also include at least one flute to clear any chips, dust, or debris generated when the anchor assembly 10 is implanted into bone tissue.

Looking again at FIGS. 1-4, the anchor assembly 10 preferably includes the locking mechanism 30. In a preferred embodiment, the locking mechanism 30 will lock the anchor assembly 10 with respect to the orthopedic device 50 thereby preventing the anchor assembly 10 from disengaging from the orthopedic device 50. The locking mechanism 30 preferably includes a locking member 32 which is configured and dimensioned to be received in an opening 34 in the anchor 11.

In a preferred embodiment, the locking member 32 has a head member 36 and a shaft member 38. The head member 36 preferably includes an opening 40 for receiving a driving instrument (not shown). The opening 40 may also include threading 42 that is capable of threadingly engaging a driving instrument for reasons explained below. In a preferred embodiment, the shaft member 38 includes at least one protrusion 44 extending along at least a portion of the circumference of the shaft member 38. Focusing on FIG. 4, at least a portion of the shaft member 38, in a preferred embodiment, also includes a hollow portion 46 which allows at least a portion of the shaft member 38 surrounding the hollow portion 46 to flex inwardly.

Turning back to FIGS. 1 and 4, the opening 34, preferably, is generally annular and extends coaxially with the longitudinal axis 12 from the head portion 14 through the neck portion 18 into the shank portion 16. The opening 34 preferably also includes at least two recesses 47, 48, each recess 47, 48 extending along at least a portion of the circumference of the opening 34. Each recess 47, 48 is configured and dimensioned to accommodate the protrusion 44.

In an exemplary use of the anchor assembly 10 with the orthopedic device 50, the orthopedic device 50 is first oriented and placed in the area of treatment. The orthopedic device 50 is then fastened to the bone tissue via at least one anchor assembly 10 which is received in at least one cavity 52 of the orthopedic device 50. Looking at FIG. 4, in a preferred embodiment, the cavity 52 has a generally spherical shape with a first diameter y at an upper portion 54. When viewed from the upper portion 54 to a lower portion 56, the diameter of the cavity 52 generally increases until approximately the middle portion of the cavity 52. The diameter of the approximately middle portion of the cavity 52 is a second diameter x. The diameter of the cavity 52 then decreases from the approximately middle portion of the cavity 52 to the lower portion 56, where the diameter of the cavity near the lower portion 56 is the same as or smaller than the first diameter y.

In a preferred embodiment, the anchor assembly 10 passes through the cavity 52 until the head portion 14 of the anchor 11 abuts the top portion 54 of the cavity 52. As can be seen in FIG. 4, in a preferred embodiment, the diameter of the head portion 14 of the anchor 11 is generally the same width as diameter x. Since the top portion 54 of the cavity 52 has a diameter y, which is smaller than the diameter x, as the head portion 14 is brought into the cavity 52, the finger elements 20 of the head portion 14 resiliently bias inwardly reducing the diameter of the head portion 14 until the head portion 14 fits through top portion 54 of the cavity 52. Once the head portion 14 passes through the top portion 54, the resilient finger elements 20 return back to their original position as the head portion 14 is seated in the cavity 52.

As best seen in FIGS. 3 and 4, in a preferred embodiment, once the anchor assembly 10 is seated in the cavity 52, the anchor assembly 10 can be locked in the cavity 52 by actuating the locking mechanism 30. In a preferred embodiment, a user actuates locking mechanism 30 by pushing on the head member 36 of the locking member 32. The downward force moves the locking member 32 further into the opening 34. As the locking member 32 moves into the opening 34, the protrusion 44 will disengage from the recess 47. Since, in a preferred embodiment, the diameter of the shaft member 38 of the locking member 32 is generally equivalent to the diameter of the opening 34 near the neck portion 18 and the shaft portion 16, the shaft member 38 will flex inwardly, aided by the hollow portion 46, to accommodate the protrusion 44 once it disengages from the recess 47. The locking member 32 will continue to move further into opening 34 until the protrusion 44 engages the recess 48 at which point the head member 36 will be seated between the resilient finger elements 20 of the head portion 14. The anchor assembly 10 is now locked in the cavity 52 since the head member 36, once seated between the resilient finger elements 20, prevents the resilient finger elements 20 from flexing inwardly. It is important to note that the disengagement of protrusion 44 from recess 47 and the engagement of the protrusion 44 with the recess 48 (and vice versa) provides the user with audible and/or tactile feedback allowing the user to quickly and easily confirm the locked or unlocked status of the anchor assembly 10.

As mentioned earlier, the head portion 36 includes the opening 40 which may include threading 42. The threading 42 in opening 40 engages a driving instrument (not shown) allowing a user to pull on the locking mechanism 30 thereby unlocking the anchor assembly 10 in the event a user wants to disengage the anchor assembly 10 from the orthopedic device 50.

In another exemplary use of the anchor assembly 10 with the orthopedic device 50, the orthopedic device 50 is first oriented and placed in the area of treatment. The orthopedic device 50 is then fastened to the bone tissue via at least one anchor assembly 10 which is received in at least one cavity 52 of the orthopedic device 50. In this exemplary use, after the anchor assembly 10 is seated in the cavity 52, but before the anchor assembly 10 is locked in the cavity 52, the anchor assembly 10 is pivoted, rotated or otherwise moved until the desired orientation with respect to the orthopedic device 50 is met. The anchor assembly 10 is then locked in place at that desired orientation by actuating the locking mechanism 30 as discussed above.

In this exemplary use, to lock the anchor assembly 10 at the desired orientation another preferred embodiment of the anchor assembly 10, and more specifically, another preferred embodiment of the locking mechanism 30 is necessary. In this preferred embodiment, the locking mechanism 30 is configured and dimensioned to resiliently bias the resilient finger elements 20 of head portion 14 outwardly when the locking mechanism 30 is pushed from the first, unlocked position, to the second, locked position. By resiliently biasing the finger elements 20 outwardly, the finger elements 20 will push against the walls of the cavity 52 thereby locking the anchor assembly 10 in place in the desired orientation. To resiliently bias the finger elements 20 outwardly, the head member 36 of the locking mechanism 30, preferably, is configured and dimensioned to include tapering surfaces and a diameter larger than the diameter of the opening 34 near the head portion 14.

Figure 5:
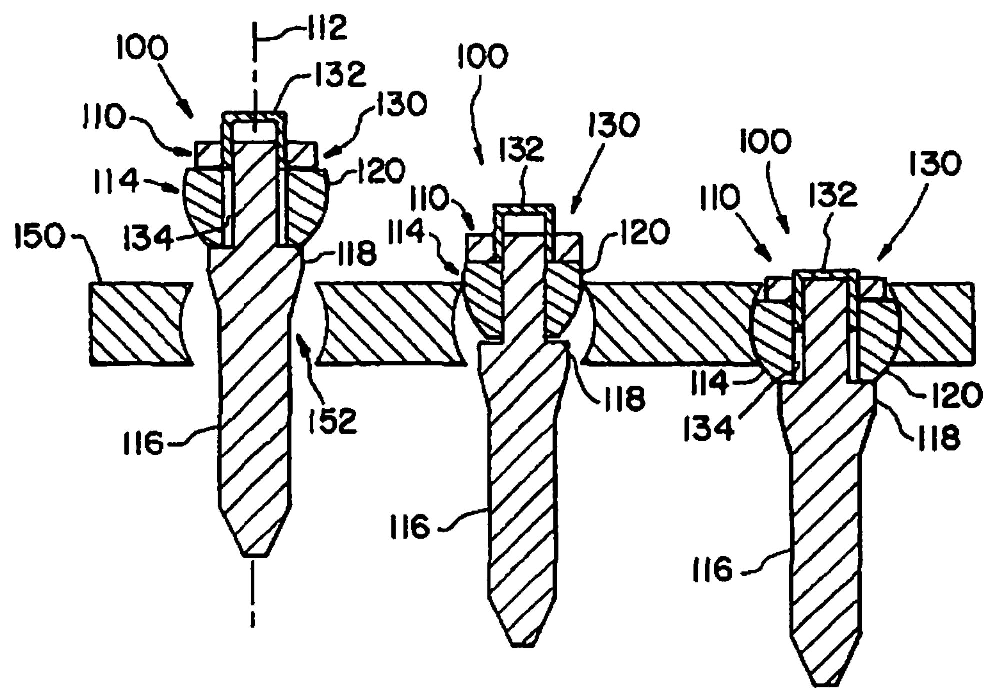
FIG. 5 is a schematic view of another embodiment of an anchor assembly being seated and locked in an orthopedic device.

Turning to FIG. 5, a preferred embodiment of the anchor assembly 100 is shown. The anchor assembly 100 is similar to anchor assembly 10, as such, only the differences between the two embodiments are addressed herein. The anchor assembly 100 preferably includes an anchor 110 and a locking mechanism 130. In a preferred embodiment, the anchor 110 includes, concentric to a longitudinal axis 112, a head portion 114, a neck portion 118 and a shank portion 116. The head portion 114 connects to the shank portion 116 through the neck portion 118. In a preferred embodiment, the head portion 114 of the anchor 110 has a generally spherical shape and includes a resilient ring element 120 captured between an upper and lower end of the head portion 114.

With continued reference to FIG. 5, in a preferred embodiment, the locking mechanism 130 will lock the anchor assembly 100 with respect to the orthopedic device 150 thereby preventing the anchor assembly 100 from disengaging from the orthopedic device 150. The locking mechanism 130 preferably includes a locking member 132 which is configured and dimensioned to be received in an opening 134 in the anchor 110.

In an exemplary use of the anchor assembly 100 with the orthopedic device 150, the orthopedic device 150 is first oriented and placed in the area of treatment. The orthopedic device 150 is then fastened to the bone tissue via at least one anchor assembly 100 which is received in at least one cavity 152 of the orthopedic device 150. In a preferred embodiment, the anchor assembly 100 passes through the cavity 152 until the head portion 114 of the anchor 110 abuts a top portion of the cavity 152. Since the top portion of the cavity 152 has a diameter that is smaller than the diameter of the head portion 114, to fit the head portion 114 into the cavity 152, the resilient ring 120 is resiliently bias inwardly, reducing the diameter of the head portion 114, until the head portion 14 fits through top portion of the cavity 152. Once the head portion 114 passes through the top portion of the cavity 152, the ring 120 returns back to its original position as the head portion 114 is seated in the cavity 152.

With continued reference to FIG. 5, in a preferred embodiment, once the anchor assembly 100 is seated in the cavity 152, the anchor assembly 100 can be locked in the cavity 152 by actuating the locking mechanism 130. In a preferred embodiment, a user actuates locking mechanism 130 by pushing on the locking member 132. The downward force moves at least a portion of the locking member 132 into opening 134. The anchor assembly 100 is now locked in the cavity 152 since the locking member 132, once seated in the opening 134, prevents the ring 120 from flexing inwardly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An assembly comprising:

an orthopedic device having a cavity; and an anchor assembly for fastening the orthopedic device to bone, the anchor assembly comprising:

a bone anchor comprising a head portion and an externally threaded shank portion integrally attached to and extending distally from the head portion along a central longitudinal axis, the head portion having a central opening surrounded by at least one resilient element, and the shank portion including a central longitudinal opening formed by an inner surface of the shank portion, wherein the inner surface includes a first recess and a second recess extending along a longitudinal edge and separated an axial distance from one another, said bone anchor is configured to be received in said cavity, such that said head portion is configured to directly engages an inner surface of said cavity; and a locking mechanism having a head member and a non-threaded shaft member, the locking mechanism is received in the central longitudinal openings extending into the head and shank portions of said bone anchor, wherein the locking mechanism incudes an annular protrusion extending around a circumference of said non-threaded shaft member of the locking mechanism for matingly engaging with said recesses in said bone anchor, and includes an enclosed hollow portion extending in said non-threaded shaft for allowing at least a portion of said non-threaded shaft member to flex inwardly to allow the annular protrusion to slide axially in the central longitudinal opening in the shank portion;

wherein said assembly has an unlocked position and a locked position to lock said anchor assembly with the orthopedic device and prevent the at least one resilient element from flexing towards the central longitudinal axis, and wherein in the unlocked position, the annular protrusion matingly engages with the first recess and the head member positioned above the head portion, and upon applying a downward force to slide the locking mechanism within the central openings of the bone anchor, the at least a portion of said non-threaded shaft member flexes inwardly disengaging the annular protrusion from the first recess and allowing the annular protrusion to matingly engages with the second recess and to seat the head member in the central opening of the head portion to prevent the at least one resilient element from flexing inwardly toward the central longitudinal axis such that the assembly is in the locked position.

2. The assembly of claim 1, wherein the orthopedic device comprises a bone plate.

3. The assembly of claim 1, wherein the head portion of the anchor includes texturing to provide friction surfaces to aid in locking the anchor assembly relative to the orthopedic device.

4. The assembly of claim 1, wherein the shank portion of the anchor assembly comprises a shaft having a generally constant diameter.

5. The assembly of claim 1, wherein the threaded shaft includes threads that decrease in diameter from a proximal end to a distal end of the shaft.

6. An assembly comprising:

an orthopedic device including a spherical cavity; and an anchor assembly received in the cavity for fastening the orthopedic device to bone, the anchor assembly comprising;

a bone anchor comprising a head portion and an externally threaded shank portion integrally attached to and extending distally from the head portion along a central longitudinal axis, the head portion having a central opening surrounded by at least one resilient element, and the shank portion including a central longitudinal opening formed by an inner surface of the shank portion, wherein the inner surface of the shank portion includes a first recess and a second recess separated an axial distance from one another, said bone anchor is configured to be received in said cavity, such that said head portion is configured for directly engaging an inner surface of said cavity; and a locking mechanism having a head member and a non-threaded shaft member, the locking mechanism is received in the central longitudinal openings extending into the head and shank portions of said bone anchor, wherein the locking mechanism includes an annular protrusion extending around a circumference of said non-threaded shaft member of the locking mechanism for matingly engaging with said recesses in said bone anchor, and includes an enclosed hollow portion extending in said non-threaded shaft for allowing at least a portion of said non-threaded shaft member to flex inwardly to allow the annular protrusion to slide axially in the central longitudinal opening in the shank portion;

wherein said assembly has an unlocked position and a locked position to lock said anchor assembly with the orthopedic device and prevent the at least one resilient element from flexing towards the central longitudinal axis, and wherein in the unlocked position, the annular protrusion matingly engages with the first recess and the head member positioned above the head portion, and upon applying a downward force to slide the locking mechanism within the central openings of the bone anchor, the at least a portion of said non-threaded shaft member flexes inwardly disengaging the annular protrusion from the first recess and allowing the annular protrusion to matingly engages with the second recess and to seat the head member in the central opening of the head portion to prevent the at least one resilient element from flexing inwardly toward the central longitudinal axis such that the assembly is in the locked position.

7. The assembly of claim 6, wherein the enclosed hollow portion is located between a proximal end and a distal end of the locking mechanism.

8. The assembly of claim 6, wherein the annular protrusion is positioned along the shaft member.

9. The assembly of claim 6, wherein the shank portion of the anchor assembly comprises a shaft having a generally constant diameter.

10. An assembly comprising:

an orthopedic device including a cavity; and an anchor assembly received in the cavity for fastening the orthopedic device to bone, the anchor assembly comprising:

an anchor comprising a spherical head portion and an externally threaded shank portion integrally attached to and extending distally from the head portion along a central longitudinal axis, the head portion having a central opening surrounded by at least one resilient element, and the shank portion including a central longitudinal opening formed by an inner surface of the shank portion, wherein the inner surface of the shank portion includes a first recess and a second recess separated an axial distance from one another, said bone anchor is configured to be received in said cavity, such that said head portion is configured for directly engaging an inner surface of said cavity; and a locking mechanism having a head member and a non-threaded shaft member, the locking mechanism received in the central longitudinal openings extending into the head and shank portions of said anchor, wherein the locking mechanism includes an annular protrusion extending around a circumference of said non-threaded shaft member of the locking mechanism for matingly engaging with said recesses in said bone anchor, and includes an enclosed hollow portion extending in said non-threaded shaft for allowing at least a portion of said non-threaded shaft member to flex inwardly to allow the annular protrusion to slide axially in the central longitudinal opening in the shank portion;

wherein said assembly has an unlocked position and a locked position to lock said anchor assembly with the orthopedic device and prevent the at lest one resilient element from flexing towards the central longitudinal axis, and wherein in the unlocked position, the annular protrusion matingly engage with the first recess and the head member positioned above the head portion, and upon applying a downward force to slide the locking mechanism within the central openings of the bone anchor, the at least a portion of said non-threaded shaft member flexes inwardly disengaging the annular protrusion from the first recess and allowing the annular protrusion to matingly engages with the second recess and to seat the head member in the central opening of the head portion to prevent the at least one resilient element from flexing inwardly toward the central longitudinal axis such that the assembly is in the locked position.

11. The assembly of claim 10, wherein the enclosed hollow portion is located between a proximal end and a distal end of the locking mechanism.

12. The assembly of claim 10, wherein the head portion of the anchor assembly is textured to provide a frictional surface.

13. The assembly of claim 10, wherein the orthopedic device comprises a bone plate.

14. The assembly of claim 10, wherein the orthopedic device comprises a spinal rod holder.

* * * * *